United States Patent
Tanner et al.

(10) Patent No.: US 6,739,201 B1
(45) Date of Patent: May 25, 2004

(54) MICROMECHANICAL APPARATUS FOR MEASUREMENT OF FORCES

(75) Inventors: Danelle Mary Tanner, Albuquerque, NM (US); James Joe Allen, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 09/665,978

(22) Filed: Sep. 20, 2000

(51) Int. Cl.[7] ................................................ G01N 3/08
(52) U.S. Cl. ........................................................ 73/826
(58) Field of Search .................... 33/706, 832; 324/662; 73/826, 514.32, 822.59, 54.01, 504.04, 514.8, 1.38; 310/307

(56) References Cited

U.S. PATENT DOCUMENTS

| | | | | |
|---|---|---|---|---|
| 4,095,903 A | * | 6/1978 | Feichtinger | 356/169 |
| 4,960,177 A | * | 10/1990 | Holm-Kennedy et al. | 177/210 C |
| 5,165,289 A | * | 11/1992 | Tilmans | 73/862.59 |
| 5,172,485 A | * | 12/1992 | Gerhard et al. | 33/706 |
| 5,355,712 A | * | 10/1994 | Petersen et al. | 73/4 R |
| 5,357,807 A | * | 10/1994 | Guckel et al. | 73/721 |
| 5,479,061 A | * | 12/1995 | Bobbio et al. | 310/309 |
| 5,583,290 A | * | 12/1996 | Lewis | 73/514.18 |
| 5,627,314 A | * | 5/1997 | Hulsing, II | 73/504.04 |
| 5,808,384 A | * | 9/1998 | Tabat et al. | |
| 6,192,757 B1 | * | 2/2001 | Tsang et al. | 73/514.32 |
| 6,361,327 B1 | * | 3/2002 | Elco et al. | 439/59 |
| 6,377,718 B1 | * | 4/2002 | Que et al. | 385/3 |

* cited by examiner

Primary Examiner—Edward Lefkowitz
Assistant Examiner—Octavia Davis
(74) Attorney, Agent, or Firm—Brian W. Dodson; John P. Hohimer

(57) ABSTRACT

A new class of micromechanical dynamometers has been disclosed which are particularly suited to fabrication in parallel with other microelectromechanical apparatus. Forces in the microNewton regime and below can be measured with such dynamometers which are based on a high-compliance deflection element (e.g. a ring or annulus) suspended above a substrate for deflection by an applied force, and one or more distance scales for optically measuring the deflection.

14 Claims, 2 Drawing Sheets

MICROMECHANICAL APPARATUS FOR MEASUREMENT OF FORCES

GOVERNMENT RIGHTS

This invention was made with Government support under Contract DE-AC04-94AL85000 awarded by the U.S. Department of Energy. The Government has certain rights in the invention.

FIELD OF THE INVENTION

The present invention relates generally to force measurement instrumentation, and more particularly to instrumentation adaptable to the special challenges of micromechanical applications.

BACKGROUND OF THE INVENTION

The development of practical micromechanical devices which can be operated reliably and manufactured routinely and with high process yield is currently hampered by a virtual absence of standard diagnostic instrumentation. Such fundamental parameters as physical structure, displacement distance, spring constants, fracture strength, forces, and many others cannot at present be measured routinely. Relative values for such parameters can at times be inferred from operating voltage, measured capacitance, and the like, but such indirect estimates fail badly when absolute accuracy is needed.

Among the practical problems generated by this lack are the difficulty of efficiently designing a set of devices which are intended to function properly and reliably with each other. Owing to process variations and independent development, a device which in its ideal design will take 8 $\mu$Newtons to operate and an actuator which ideally will deliver 12 $\mu$Newtons may not function properly together when integrated into and fabricated on a single chip. Modification of the fabrication process also can result in unexpected changes in functionality for complex devices. The ability to measure absolute fundamental material and device properties would greatly reduce the time and expense required to make such adjustments.

Several approaches exist to estimate relative forces in specific situations. For example, for a parallel plate electrostatic actuator, the output force can be estimated given the area of the plates, the voltage difference between the plates, and the distance between the plates. In most cases, this works fairly well for large plates and near-zero displacements. However, because no technique exists to directly calibrate the force produced by such an actuator, many potentially defective assumptions must be made to calculate the actuator force. Among these are that the areas for the plates are correct, that the plates are flat, that the plates are parallel, that the plate supports have not warped from residual stress (which could change the plate's separation at rest), that doping or interlayer electrical difficulties do not reduce the voltage or charge being applied to the plates, and so on. With most of these problems, the actuator will give 4 times the force when twice the voltage is applied, so relative measurements can be made using this approach, but absolute measurements do not presently appear practical.

Another approach which has been used is to measure the bending of a cantilever under an applied force. The equations describing the bending of a cantilever are then used to extract the force being applied. This approach has a number of problems. As before, assumptions concerning the dimensions and structure of the cantilever and its anchor have to be made to do the analysis.

Beyond that, the strain acting on a bent cantilever is highly inhomogeneous owing to the stress concentration associated with the cantilever anchor. The response of the cantilever therefore depends sensitively on structural flaws, particularly those which may exist near the anchoring structure.

Also, the strains encountered in making practical force measurements in the realm of micromechanical devices are a sufficiently large that the material from which the cantilever and at least part of its support are made exhibit nonlinear mechanical responses. This factor complicates the analysis, and makes the measurement even more susceptible to process variations and similar unintended factors.

Accordingly, there is a long-felt need for a micromechanical device which can measure absolute forces with reasonable accuracy. Ideally, such a device would be integrable with production microelectromechanical systems (MEMS), and could be calibrated independent of other MEMS devices. Further, interpreting the output of such a device would be simplified if the basic design required limited material strain for operation. Finally, real-time diagnostics for proper functioning of the device would be useful.

SUMMARY OF THE INVENTION

A new class of micromechanical dynamometers is disclosed. The combination of the small size scale and the enormous strength of micromechanical materials allows a wide range of applied forces to be measured directly. These dynamometers can be externally calibrated against a reference.

DETAILED DESCRIPTION

Figure 1:
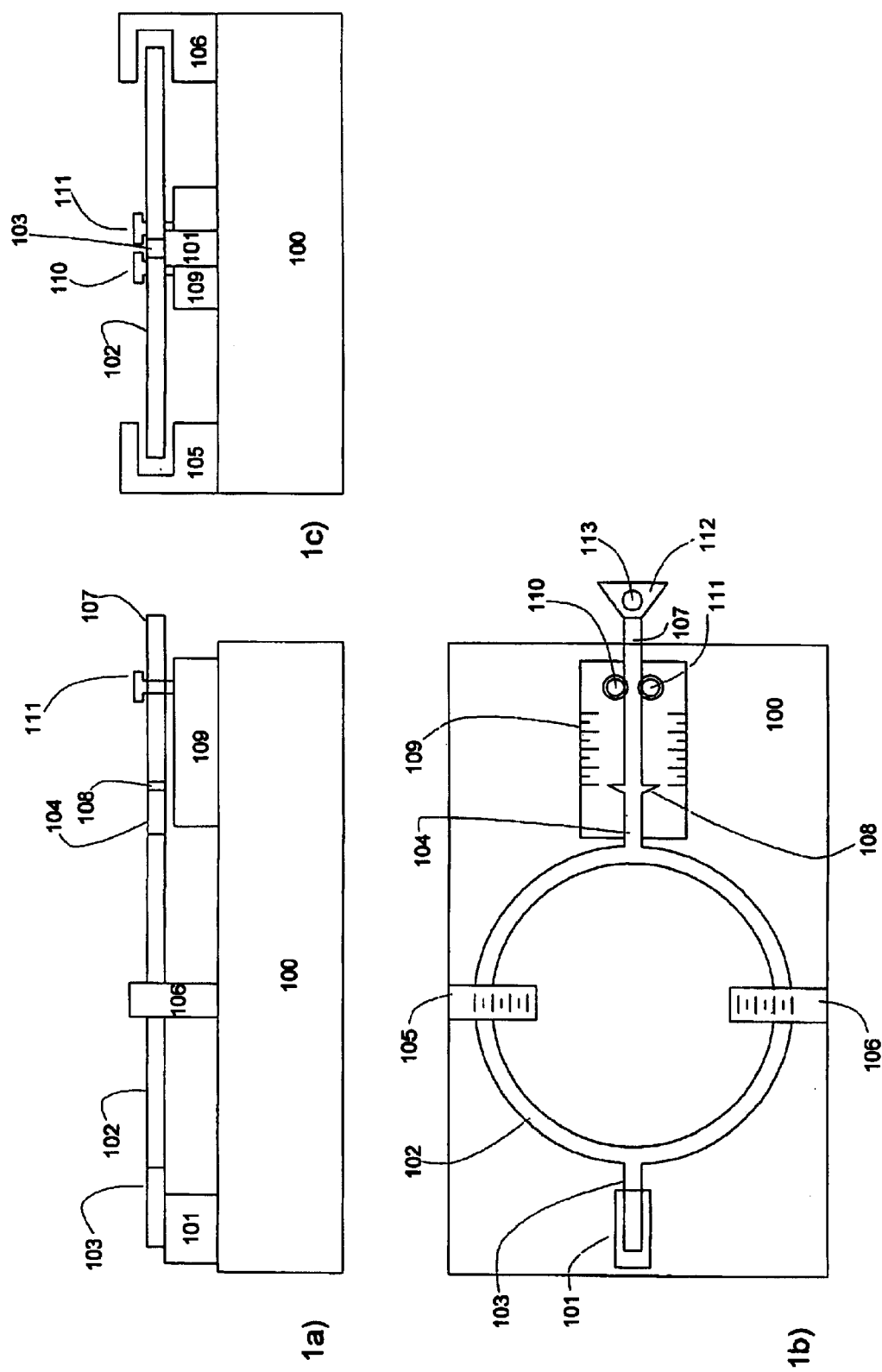
FIG. 1. Side (1a) top (1b), and front (1c) views of a micromechanical dynamometer after the instant invention.

A specific implementation of a micromechanical dynamometers after the instant invention appears in FIG. 1, where FIG. 1a is the side view, FIG. 1b is a top view, and FIG. 1c is a front view of the dynamometer.

Anchor 101 is located on substrate 100. A deflection element comprising anchor site 103, stress deformation ring 102, and input site 104, is then affixed to anchor 101. As shown, the stress deformation ring 102 is essentially parallel to the surface of substrate 100. Ring constraints 105 and 106 comprise a notch within which ring 102 is free to move, and as shown also comprise a distance scale, so that deformation of ring 102 in response to forces applied to input site 104 can be optically measured.

Force coupler 107 (in this case a simple rod) allows a convenient connection to forces generated external to the dynamometer, and comprises indicator 108, which indicates the amount of stretching of ring 102 in response to such external force. Force coupler 107 moves within the constraint of motion guides 110 and 111, which are mounted on scale body 109, which also comprises a distance scale for quantitative optical measurement of ring 102 stretching. Force coupler 107 can also comprise a calibration force input, which comprises a hole 113 in an extension 112 of force coupler 107, said hole being suitable for applying a calibration force using a nanoindenter or similar external equipment.

The dynamometer shown in FIG. 1, and many variations thereof, can conveniently be fabricated from a series of patterned thin film layers along with microelectromechanical devices. Materials which can be used in such apparatus include crystalline silicon, polysilicon, amorphous silicon, silicon oxide, silicon nitride, amorphous diamond, sol-gel glasses.

In use, an external force is coupled to force coupler 107. The external force will be assumed to pull force coupler 107 away from ring 102. In response to this force, the diameter of ring 102 along the axis of force coupler 107 increases, and the diameter of ring 102 perpendicular to that axis decreases. The changes in these diameters can be determined by optical inspection of the distance scales. The resulting displacement measurements can then be converted into a force magnitude by using a calibration equation.

Figure 2:
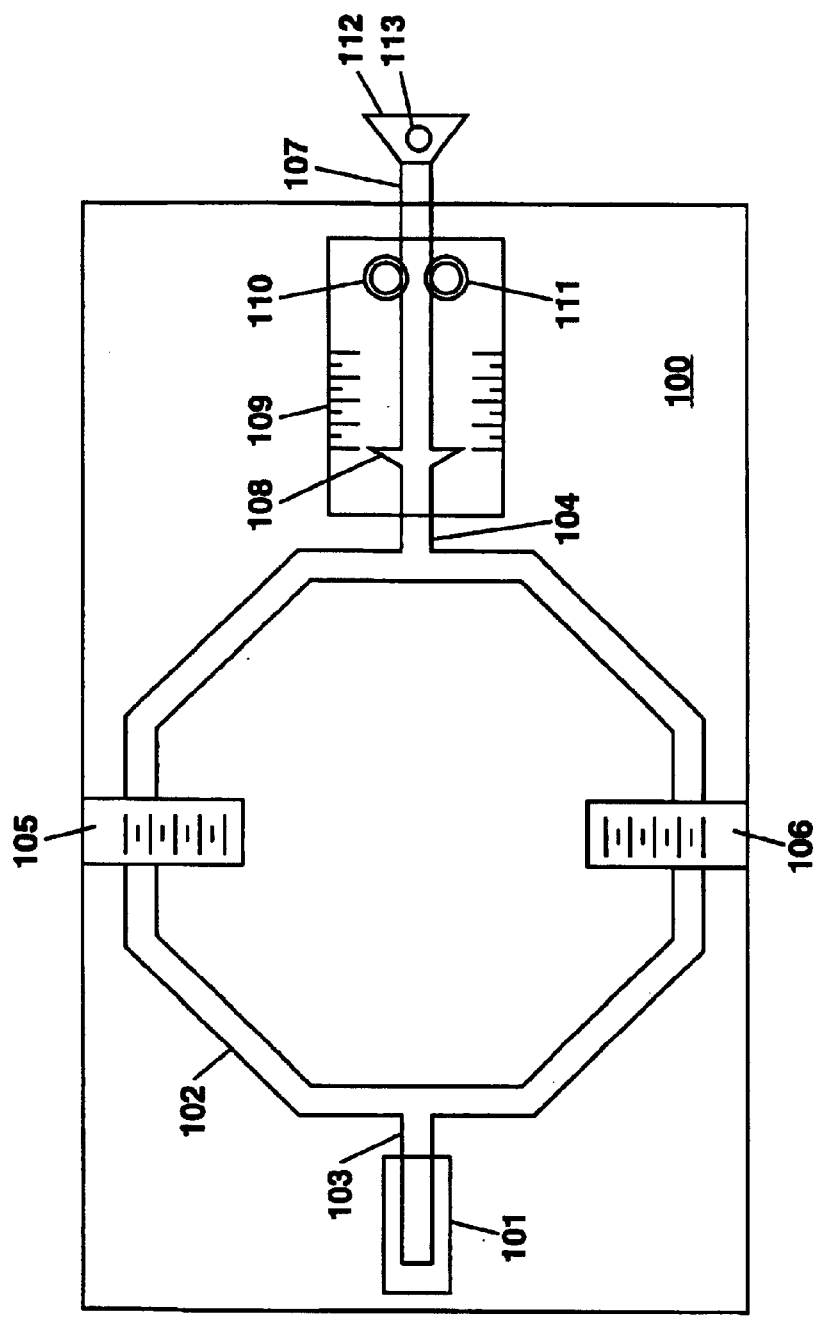
FIG. 2. A schematic top view of another embodiment of the instant invention with the deflection element having a polygonal ring structure.

The deflection element, comprising a set of anchor sites and a set of input sites, is preferably a high-compliance deflection element. By high-compliance is meant that the deflection element has an effective spring constant much smaller than that of an equivalent solid deflection element. In essence, the holes and other features introduced into a high-compliance deflection element introduce low-stiffness bending modes into an otherwise solid deflection element, and these low-stiffness bending modes dramatically decrease the effective spring constant. For example, in the implementation of FIG. 1, the ring 102 can easily elongate under applied stress—typically orders of magnitude more easily than if the ring were replaced by a solid disk. Note that many shapes and configurations beside the annulus or ring can be used to obtain a high-compliance deflection element. For example, FIG. 2 shows a high-compliance deflection element having the shape of a regular polygon.

What is claimed is:

1. A micromechanical dynamometer, comprising:
   a) a substrate;
   b) a ring-shaped high-compliance deflection element comprising at least one anchor site and at least one input site;
   c) one anchor for each anchor site, extending between the substrate and said anchor site;
   d) a force coupler transferring force from an external source to the at least one input site; and,
   e) at least one distance scale for optically measuring a deflection of the high-compliance deflection element in response to the force provided from the external source, with the distance scale being functionally attached to the high-compliance deflection element.

2. The dynamometer of claim 1, wherein the high-compliance deflection element comprises crystalline silicon, polycrystalline silicon, amorphous silicon, silicon oxide, silicon nitride, amorphous diamond, or a sol-gel glass.

3. The dynamometer of claim 1, wherein the high-compliance deflection element comprises an annulus of material, said annulus having the shape of a polygon, and essentially constant thickness normal to said polygon.

4. The dynamometer of claim 3, wherein said high-compliance deflection element has a line of mirror symmetry.

5. The dynamometer of claim 3, wherein said polygon is a regular polygon.

6. The dynamometer of claim 1, wherein the high-compliance deflection element comprises a circular annulus having a rectangular cross-section of essentially constant dimensions throughout.

7. The dynamometer of claim 1, wherein each distance scale operates in combination with an indicator which is mechanically coupled to a displacement of the high-compliance deflection element.

8. The dynamometer of claim 7, wherein each indicator is coupled to a different point on the deflection element.

9. The dynamometer of claim 7, wherein each distance scale is optically readable so that displacement of the indicator can thereby be quantified optically.

10. The dynamometer of claim 1, further comprising a calibration force input.

11. The dynamometer of claim 10, wherein the calibration force input is integral with the force coupler.

12. The dynamometer of claim 1, further comprising a deflection element restraint system.

13. The dynamometer of claim 12, wherein said restraint system comprises motion guides.

14. The dynamometer of claim 13, wherein said restraint system comprises ring constraints.

* * * * *